(12) United States Patent
Heiskanen et al.

(10) Patent No.: US 10,752,741 B2
(45) Date of Patent: Aug. 25, 2020

(54) UV BLOCKING FILM AND COMPOSITION COMPRISING MICROFIBRILLATED CELLULOSE, A METHOD FOR PRODUCING SAID FILM AND USE OF THE COMPOSITION

(71) Applicant: Stora Enso OYJ, Helsinki (FI)

(72) Inventors: Isto Heiskanen, Imatra (FI); Katja Lyytikäinen, Imatra (FI); Esa Saukkonen, Lappeenranta (FI); Kaj Backfolk, Villmanstrand (FI)

(73) Assignee: Stora Enso, OYJ, Helsinki (FI)

( * ) Notice: Subject to any disclaimer, the term of this patent is extended or adjusted under 35 U.S.C. 154(b) by 31 days.

(21) Appl. No.: 16/302,813

(22) PCT Filed: May 15, 2017

(86) PCT No.: PCT/IB2017/052856
§ 371 (c)(1),
(2) Date: Nov. 19, 2018

(87) PCT Pub. No.: WO2017/199157
PCT Pub. Date: Nov. 23, 2017

(65) Prior Publication Data
US 2019/0292337 A1 Sep. 26, 2019

(30) Foreign Application Priority Data
May 20, 2016 (SE) .................................... 1650690

(51) Int. Cl.
| | |
|---|---|
| C08J 5/18 | (2006.01) |
| A61K 8/73 | (2006.01) |
| A61Q 17/04 | (2006.01) |
| C08J 5/04 | (2006.01) |
| C09D 5/32 | (2006.01) |
| D21H 11/02 | (2006.01) |
| D21H 11/08 | (2006.01) |
| D21H 11/18 | (2006.01) |
| D21H 21/16 | (2006.01) |
| D21H 19/34 | (2006.01) |
| C08L 1/02 | (2006.01) |
| D21H 19/52 | (2006.01) |
| D21H 11/12 | (2006.01) |
| A61K 8/02 | (2006.01) |
| D21H 19/38 | (2006.01) |
| D21H 21/14 | (2006.01) |
| D21H 17/67 | (2006.01) |
| D21H 11/10 | (2006.01) |

(52) U.S. Cl.
CPC ............... C08J 5/18 (2013.01); A61K 8/027 (2013.01); A61K 8/731 (2013.01); A61Q 17/04 (2013.01); C08J 5/045 (2013.01); C08L 1/02 (2013.01); C09D 5/32 (2013.01); D21H 11/02 (2013.01); D21H 11/08 (2013.01); D21H 11/10 (2013.01); D21H 11/12 (2013.01); D21H 11/18 (2013.01); D21H 19/34 (2013.01); D21H 19/52 (2013.01); D21H 21/16 (2013.01); A61K 2800/412 (2013.01); A61K 2800/413 (2013.01); C08J 2301/02 (2013.01); D21H 17/675 (2013.01); D21H 19/385 (2013.01); D21H 21/143 (2013.01)

(58) Field of Classification Search
CPC ................................ D21H 11/10; C08L 1/02
See application file for complete search history.

(56) References Cited

U.S. PATENT DOCUMENTS

| | | | |
|---|---|---|---|
| 6,183,596 B1 | 2/2001 | Matsuda et al. | |
| 6,432,517 B1* | 8/2002 | Yokota ................... | B41M 5/502 428/32.21 |
| 2011/0081554 A1* | 4/2011 | Ankerfors .............. | D21H 17/25 428/535 |
| 2011/0259537 A1* | 10/2011 | Husband ................. | D21B 1/30 162/4 |
| 2011/0277947 A1* | 11/2011 | Hua ....................... | D21H 21/10 162/28 |
| 2012/0136146 A1* | 5/2012 | Heiskanen ............. | D21C 9/007 536/56 |
| 2012/0316330 A1* | 12/2012 | Zhu ........................ | B82Y 40/00 536/56 |
| 2013/0000855 A1* | 1/2013 | Nuopponen ........... | D21H 11/18 162/76 |

(Continued)

FOREIGN PATENT DOCUMENTS

| | | |
|---|---|---|
| EP | 2653508 A1 | 10/2013 |
| JP | 2013194192 | 9/2013 |
| JP | 2016056460 | 4/2016 |
| WO | 2008140337 A1 | 11/2008 |
| WO | 2011059398 A1 | 5/2011 |
| WO | 2012097446 A1 | 7/2012 |

OTHER PUBLICATIONS

Hubbe (Paper, Kirk-Othmer Encyclopedia of Chemical Technology, vol. 17, 2005) (Year: 2005).*
International Search Report for PCT/IB2017/052856, dated Jul. 7, 2017.
Osong S.H. et al., "Paper strength improvement by inclusion of nano-ligno-cellulose to Chemi-thermomechanical pulp" Nordic Pulp & Paper Research Journal, 2014, pp. 309-316, vol. 29, No. 2.
Spence, K.L., "The effect of chemical composition on microfibrillar cellulose films from wood pulps: Mechanical processing and physical properties" Bioresource Technology, 2010, pp. 5961-5968, vol. 101.

(Continued)

Primary Examiner — Liam J Heincer
(74) Attorney, Agent, or Firm — Greer, Burns & Crain, Ltd.

(57) ABSTRACT

The present invention relates to an UV blocking film comprising microfibrillated cellulose wherein at least part of the microfibrillated cellulose is microfibrillated cellulose produced from non-chemical modified lignocellulosic material. The invention also relates to a method for producing the film, use of said film as well as a composition having UV blocking properties.

22 Claims, 1 Drawing Sheet

(56) References Cited

U.S. PATENT DOCUMENTS

| | | | | |
|---|---|---|---|---|
| 2013/0017394 | A1* | 1/2013 | Hua | D21D 1/20 |
| | | | | 428/401 |
| 2013/0025920 | A1* | 1/2013 | Shimizu | C08J 3/09 |
| | | | | 174/258 |
| 2013/0047893 | A1* | 2/2013 | Heiskanen | C09D 101/02 |
| | | | | 106/447 |
| 2013/0053454 | A1* | 2/2013 | Heiskanen | C09D 101/02 |
| | | | | 514/781 |
| 2013/0056165 | A1* | 3/2013 | Kilpelainen | D21H 11/18 |
| | | | | 162/9 |
| 2013/0284387 | A1* | 10/2013 | Umemoto | C08J 5/045 |
| | | | | 162/9 |
| 2014/0073774 | A1* | 3/2014 | Heiskanen | C02F 11/006 |
| | | | | 536/56 |
| 2014/0124150 | A1* | 5/2014 | Sabourin | D21C 9/001 |
| | | | | 162/9 |
| 2014/0338849 | A1* | 11/2014 | Kosonen | C08B 15/04 |
| | | | | 162/1 |
| 2015/0017432 | A1 | 1/2015 | Shoseyov et al. | |
| 2015/0114581 | A1* | 4/2015 | Kinnunen | B32B 5/26 |
| | | | | 162/125 |
| 2015/0148460 | A1* | 5/2015 | Senba | C08L 1/02 |
| | | | | 524/35 |
| 2015/0218757 | A1* | 8/2015 | Heiskanen | D21C 5/005 |
| | | | | 162/9 |
| 2015/0315747 | A1* | 11/2015 | Heiskanen | D21H 11/18 |
| | | | | 162/181.2 |
| 2015/0337493 | A1* | 11/2015 | Heiskanen | C08L 1/04 |
| | | | | 162/9 |
| 2016/0145805 | A1* | 5/2016 | Kroener | D21B 1/08 |
| | | | | 162/4 |
| 2016/0237621 | A1* | 8/2016 | Cutts | D21H 21/10 |
| 2017/0320509 | A1* | 11/2017 | Axrup | C08B 1/00 |
| 2018/0037737 | A1* | 2/2018 | Semba | C08J 5/045 |
| 2019/0024318 | A1* | 1/2019 | Backfolk | D21H 17/29 |
| 2019/0024320 | A1* | 1/2019 | Hakansson | D21H 17/675 |
| 2019/0234020 | A1* | 8/2019 | Backfolk | D21H 11/18 |
| 2019/0276621 | A1* | 9/2019 | Heiskanen | C08J 5/18 |

OTHER PUBLICATIONS

Qian, Y. "Lignin: a nature-inspired sun blocker for broad-spectrum sunscreens" Green Chemistry, Sep. 2015, pp. 320-324, vol. 17.

Hambardzumyan, Arayik, et al., "Natural Organic UV-Absorbent Coatings Based on Cellulose and Lignin: Designed Effects of Spectroscopic Properties," Biomacromolecules, 2012, 13, 4081-4088.

Kojima, Yoichi, et al., "Reinforcement of Wood Flour Board Containing Ligno-Cellulose Nanofiber Made From Recycled Wood," Journal of Wood Science, 2015, 61, 492-499.

\* cited by examiner

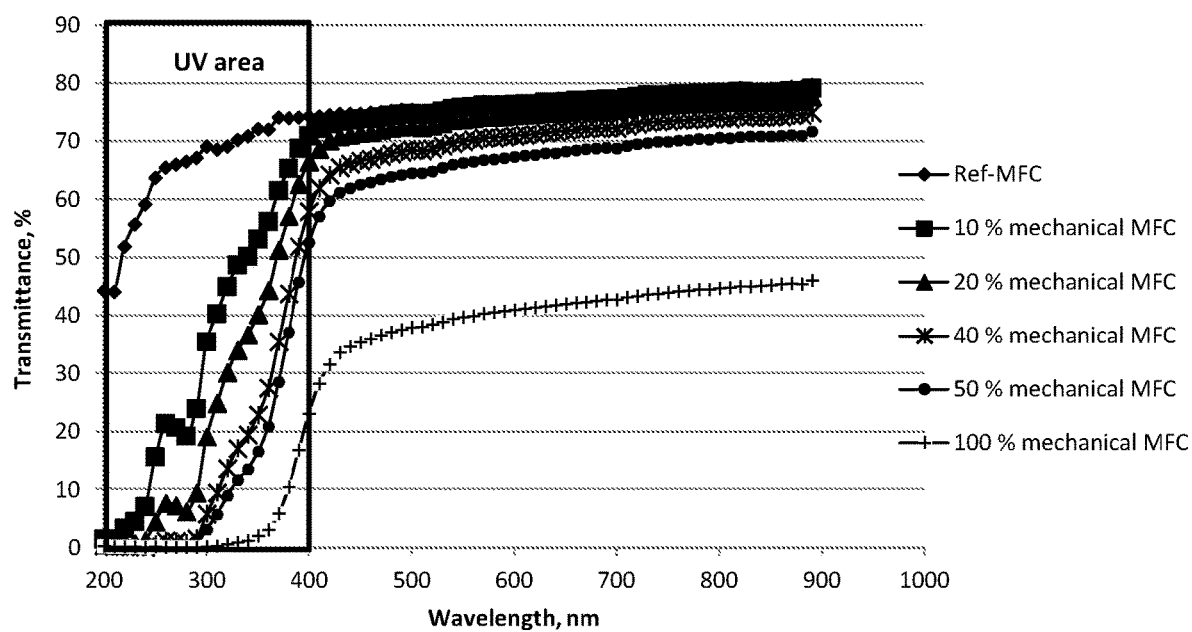

UV BLOCKING FILM AND COMPOSITION COMPRISING MICROFIBRILLATED CELLULOSE, A METHOD FOR PRODUCING SAID FILM AND USE OF THE COMPOSITION

This application is a U.S. National Phase under 35 U.S.C. § 371 of International Application No. PCT/IB2017/052856, filed May 15, 2017, which claims priority under 35 U.S.C. §§ 119 and 365 to Swedish Application No. 1650690-9, filed May 20, 2016.

TECHNICAL FIELD

The present invention relates a film having good UV resistance and a good oxygen transmission rate (OTR) value. The invention further relates to a method for producing said film and a composition with UV blocking properties.

BACKGROUND

The amount of UV radiation from the sun that reaches the surface of the earth varies around the globe and through time. Several factors account for this variation, e.g. cloud cover or ozone layer. UV (ultraviolet) radiation is light with wavelengths shorter than those visible to the human eye. UV radiation is divided into three categories by wavelengths: UVA (320-400 nm), UVB (290-320 nm) and UVC (100-290 nm). The wavelengths of UVA are longer than UVB and can penetrate deeper into the layers of our skin. UVA radiation contributes to skin aging, photochemical smog, fading and damage to woods, plastics, paints and fabrics. Only 1% of the solar radiation is within the UVB band, and most of this is blocked by the ozone layer. Nevertheless, UVB wavelengths are those that can cause the most damage to human skin. UVC radiation is totally blocked by the ozone and other gases in the atmosphere, and does not reach the surface of the earth.

UV radiation has both positive and negative effects. However, due to the negative impact that UV radiation sometimes has it is important to find solutions how to prevent the UV radiation to cause damages. The most common solution is to use UV blockers that will block the UV radiation and thus reduces the UV degradation of the exposed material. UV blockers are often used as additives in window films, in paints, coatings, plastic or plastic films, sunscreens and in paper or paperboard products. Components used as UVA/UVB blockers are e.g. avobenzone, oxybenzone, titanium dioxide and zinc oxide and they will prevent e.g. the skin or material from being negatively affected by the UV radiation. However, the UV blockers used today are both costly and might also have a negative effect on the environment or might not be approved for use in certain applications.

Thus, there is a need for a more environmental friendly and cost efficient UV blocker.

SUMMARY

It is an object of the present invention, to provide a film comprising microfibrillated cellulose produced from non-chemical modified lignocellulosic material, which film has good UV blocking properties at the same time as the oxygen transmission rate (OTR) values are good especially at high moisture contents. Another object of the present invention is to produce a film with UV blocking properties in a good way. Yet another object of the present invention is a composition having UV blocking properties which composition comprises non-chemical modified lignocellulosic material as well as use of said composition.

The invention is defined by the appended independent claims. Preferred embodiments are set forth in the appended dependent claims and in the following description and drawings.

The present invention relates to an UV blocking film comprising microfibrillated cellulose (MFC) wherein at least part of the microfibrillated cellulose is microfibrillated cellulose produced from non-chemical modified lignocellulosic material.

It has surprisingly been found that an UV film comprising microfibrillated cellulose produced from non-chemical modified lignocellulosic material can be used in order to give the MFC film good UV blocking properties at the same time as the MFC film will be transparent or at least semi-transparent or translucent, i.e. the presence of MFC from the non-chemical modified lignocellulosic material will still make it possible to produce transparent films with good OTR values at high moisture contents. The use of MFC from non-chemical modified lignocellulosic material as an UV blocker has many advantages. First of all MFC from non-chemical modified lignocellulosic material is a renewable material which makes it much more environmental friendly compared to UV blockers most commonly used today. Furthermore, MFC from non-chemical modified lignocellulosic material is quite cost efficient and it is also a safe material to handle, i.e. there are no health risks with handling the MFC from non-chemical modified lignocellulosic material during the production and use. There are already today non-chemical modified lignocellulosic materials that are approved in e.g. food applications or for direct skin contact applications, i.e. it is considered to a safe material. Also, the MFC from non-chemical modified lignocellulosic material tends to absorb less water making the film more moisture resistance.

The non-chemical modified MFC is preferably produced from mechanical pulp which can be chemithermomechanical pulp (CTMP), thermomechanical pulp (TMP), pressure groundwood (PGW) pulp and/or stone groundwood pulp (SGP).

The non-chemical modified lignocellulosic material may be fiber from a coconut shell.

The film preferably comprises between 2.5-50% by weight of the fiber based material of microfibrillated cellulose produced from non-chemical modified lignocellulosic material, preferably between 5-40% by weight or even more preferably between 5-20% by weight. It has surprisingly been found that it is sufficient that the MFC film comprises small amounts of MFC from non-chemical modified lignocellulosic material, preferably mechanical MFC, in order for the film to have good UV blocking properties. When producing a film comprising MFC there is a desire to produce a film having good UV blocking properties, which can be seen as a low transmittance (%) in the UV area. The film should at the same time be transparent or at least semi-transparent, which can be seen as a high transmittance (%) in the visible light area, i.e. at higher wave lengths compared to the UV wave lengths. This is normally not easy to achieve and definitely not in an easy, cost efficient and environmental friendly way.

The film may also comprise microfibrillated cellulose produced from chemical modified lignocellulosic material, preferably MFC from chemical pulp.

The film preferably comprises 50-97.5% by weight of fiber based material of microfibrillated cellulose produced from chemical modified lignocellulosic material, preferably MFC from chemical pulp, preferably between 60-95% by weight or even more preferred between 80-95% by weight. Chemical MFC has the advantage that it gives the MFC film good barrier properties, especially good oxygen barrier properties. Also, the presence of chemical MFC will improve the film forming properties of the film. Furthermore, the use of chemical MFC will also make the MFC film more transparent compared to if mechanical MFC were used. Yet another advantage with the present invention is that the production of chemical MFC is quite cost effective.

The film may also comprise nano-fillers, preferably nano-precipitated calcium carbonate (PCC), nano-fillers from bentonite, nano-fillers from titanium dioxide, nano-fillers from zinc oxide, nanotalc, nano clays and/or other nano sized fillers.

The film preferably has a basis weight of less than 50 g/m$^2$, or less than 35 g/m$^2$, or less than 25 g/m$^2$.

The film preferably has a transmittance of at least 70% for radiation with wavelengths above 400 nm meaning that the film is translucent or transparent for the human eye (in the visible light area). The film preferably has a transmittance below 70% for radiation with wavelengths below 400 nm meaning that the film blocks radiation within the UV area.

The present invention also relates to a method for manufacturing a film having UV blocking properties wherein the method comprises the steps of; providing a first suspension comprising microfibrillated cellulose produced from non-chemical modified lignocellulosic material, conducting the first suspension to a wire and dewatering the first suspension to form a film.

The method may also comprise the steps of; providing a second suspension comprising microfibrillated cellulose produced from chemical modified lignocellulosic material, mixing the first and second suspension whereby a mixture is obtained and thereafter conducting the mixture to a wire and thereafter dewatering the mixture to form the film. The first suspension is thus conducted to the wire as a mixture together with the second suspension.

The microfibrillated cellulose preferably has a Schopper Riegler value (SR°) of more than 87 SR°, preferably more than 90 SR°, more than 93 SR°, or more than 95 SR°.

The mixture obtained in the method according to the present invention preferably comprises the first suspension in an amount of 2.5-50% by weight of the total weight of the mixture and the second suspension in an amount of 50-97.5% by weight of the total weight of the mixture.

Nano-filler, preferably nano-precipitated calcium carbonate (PCC) is added to the first suspension and/or second suspension. Other nano-fillers such as nano-fillers from bentonite, nano-fillers from titanium dioxide, nano-fillers from zinc oxide, nanotalc, nano clays and/or other nano sized fillers may also be added.

The present invention also relates to a composition having UV blocking properties wherein said composition comprises microfibrillated cellulose produced from non-chemical modified lignocellulosic material. It has surprisingly been found that MFC from non-chemical modified lignocellulosic material, preferably mechanical MFC, can be used in compositions and giving the composition UV blocking properties.

The composition preferably comprises 2.5-50% by weight of fiber based material of microfibrillated cellulose produced from non-chemical modified lignocellulosic material, preferably between 5-40% by weight and even more preferred between 5-20% by weight. It has been found that it is sufficient to add small amounts of MFC from non-chemical modified lignocellulosic material, preferably mechanical MFC, to a composition and the composition will still have very good UV blocking properties.

The composition may be a paint, a sunscreen, a coating color, a sizing composition, a yarn, a composite comprising a polymer used for e.g. screw caps or a wood impregnation solution.

The present invention also relates to the use of the film describes above as a window film, on the surface of a paper or paperboard product or as a mulch or laminated onto a mulch.

BRIEF DESCRIPTION OF THE DRAWINGS

FIG. 1 is a graph of transmittance as a function of wavelength.

DETAILED DESCRIPTION

With UV blocking film is meant that the film is blocking radiation within the UV range, i.e. radiation with wavelengths between 100-400 nm including both UVA and UVB radiation. The UV blocking film according to the invention blocks at least 65% of the UV radiation at a thickness of about 20 um.

With lignocellulosic material is meant a material comprising lignin, cellulose and hemicellulose. The lignocellulosic material is preferably a cellulose material, i.e. a hardwood and/or softwood wood material. The lignocellulosic material may also be a bagasse, bamboo, corn cobs, corn stovers, fibers from coconut shells or other lignocellulosic material.

MFC produced from non-chemical modified lignocellulosic material means that the production of MFC is done from a lignocellulosic material that has not been chemically modified prior to the MFC production, meaning that the lignocellulosic material has not been modified with any chemical that degrades the lignocellulosic material excluding any normal treatment used in pulp production, i.e. digesting, use of chelating agents and/or bleaching of the fibers. The production of MFC from the non-chemical modified lignocellulosic material can then be produced in any conventional matter, i.e. by mechanical, enzymatic and/or chemical treatments wherein the chemical treatment is only done to facilitate the mechanical fibrillation of the fibers, e.g. swelling of the fibers etc.

It is preferred that the MFC produced from non-chemical modified lignocellulosic material is MFC produced from mechanical pulp. Mechanical pulp means pulp produced by subjecting wood fibers to mechanical energy causing the bonds between the fibers of the wood to break and fibers and fiber fragments to be released. In the definition of mechanical pulp is groundwood pulp, e.g. stone groundwood pulp (SGP) or pressure groundwood (PGW) pulp, as well as thermomechanical pulp (TMP) or chemimechanical pulp (CTMP) included. The MFC from mechanical cellulosic pulp is referred to as mechanical MFC.

With chemical modified lignocellulosic material is meant lignocellulosic material that has been chemically modified with at least one chemical where said chemical degrades the lignocellulosic material. The chemical modified lignocellulosic material is preferably chemical pulp, i.e. the MFC from chemical modified lignocellulosic material is preferably MFC made from chemical pulp, e.g. kraft pulp or sulfite pulp in any known way, e.g. by enzymatic, mechanical and/or chemical treatments, also referred to as chemical MFC.

It has surprisingly been found that microfibrillated cellulose produced from non-chemical modified lignocellulosic material, preferably mechanical pulp, has the ability to block UV radiation. Even more surprising is that small amounts of microfibrillated cellulose produced from non-chemical modified lignocellulosic material are sufficient in order to achieve good UV properties in e.g. a film or a composition. The reason to why the MFC from non-chemical modified lignocellulosic material has UV blocking properties is not fully understood. One theory is that microfibrillated cellulose produced from non-chemical modified lignocellulosic material comprises all elements of wood, i.e. no elements have been removed unlike chemical MFC, and one or more of these elements gives the mechanical MFC UV blocking properties. Also, all elements of wood, such as lignin, are bound in the microfibrils of the mechanical MFC. In this way the MFC from non-chemical modified lignocellulosic material, preferably mechanical MFC, is a much safer compound to use as UV blocker compared to if the elements giving the UV blocking properties were added separately to a composition or in a film.

The MFC film according to the invention is transparent or semi-transparent making it suitable for many different end uses. For some paper or paperboard products, e.g. products made from Solid Bleached Sulphate (SBS) pulp, it is necessary to improve the UV properties of the product preventing either the paper or paperboard per se and/or the product packed in a package produced by the paper or paperboard from being affected by the UV radiation. Thus, it is both possible to add a composition comprising the mechanical MFC to a paper or paperboard furnish, a coating color, sizing composition or to laminate or extrude a MFC film comprising the mechanical MFC to the surface of the paper or paperboard and thus improving the UV blocking properties of the paper or paperboard product. Furthermore, the MFC film according to the invention will have good OTR values even at high moisture contents which make it suitable for end uses in high moisture environments, e.g. for liquid packaging boards or for packages used in hotter climates having high humidity.

The film preferably has a transmittance of at least 70% for radiation with wavelengths above 400 nm meaning that the film is translucent or transparent for the human eye (in the visible light area). The film preferably has a transmittance below 70% for radiation with wavelengths below 400 nm meaning that the film blocks radiation within the UV area. By the present invention it is thus possible to produce a film that blocks UV radiation but still is transparent in the visible light area. The transmittance could be measured with any suitable spectrometer, e.g. Cary 100 Conc spectrophotometer with DRA CA-301 Integrating Sphere, at room temperature and at a relative humidity of 50%.

It has been found advantageous to use MFC produced from non-chemical modified fibers from coconut shell in the film since the coconut fibers had very good UV blocking properties at the same time as they are normally FDA approved, i.e. approved for use in food packages.

The MFC film having UV blocking properties is produced by providing a first suspension comprising microfibrillated cellulose produced from mechanical pulp, conducting the first suspension to a wire and thereafter dewatering the first suspension to form a film. The dewatering may be done on the wire or in subsequent conventional dewatering equipment. It may be preferred that the MFC film also comprises chemical MFC. Thus, the method to produce the film may also comprise the steps of providing a second suspension comprising microfibrillated cellulose produced from chemical pulp, mixing the first and second suspension whereby a mixture is obtained, conducting the mixture to a wire and thereafter dewater the mixture to form the film. Thus, the first suspension comprising mechanical MFC is conducted to a wire and dewatered together with the second suspension as a mixture.

The first suspension or the mixture may be provided onto a porous wire of a paper making machine to form a web, i.e. any kind of paper making machine known to a person skilled in the art used for making paper, paperboard, tissue or any similar products. The formed web is then dewatered and may then subsequently be dried to form a film. Any conventional dewatering or drying equipment may be used.

The film formed may be then be calendered. The final density, film properties and moisture content may thus be adjusted in the calendar. Known techniques such as hard-nip, soft-nip, soft-hard nip, cylinder or belt, in various forms and combinations can be used.

The MFC film may also comprise other UV blocking additives, such as benzotriazole based organic compounds, titanium dioxide, zinc oxide etc. Depending on the end use of the MFC film according to the invention it might be necessary to even further improve the UV blocking properties of the film by adding other commonly used UV blocking additives. However, the use of mechanical MFC reduces the use/need of other additives which makes it possible to use lower amounts of other UV blocking additives which both makes it more cost efficient as well as environmental friendly.

The MFC film according to the invention may be used in free standing pouches, packages for dairy products or fatty food. It may also be used as a layer on a paper or paperboard substrate to improve the UV blocking properties of a paper or paperboard product. It can also be used as a window film to reduce the UV radiation through windows.

The composition comprising microfibrillated cellulose produced from mechanical pulp may be a paint. With paint means a liquid that converts to a solid film after a thin layer of the paint has been applied to a substrate. Primers, lacquers or colored paints are including in the definition of paint. The presence of the mechanical MFC in the paint does not only give the paint UV resistance properties but it also has the advantage that it increases the viscosity of the paint. Normally additives for improving the viscosity are added to paint compositions in order for the paint to get the necessary viscosity. By using mechanical MFC as an additive in the paint both improved UV resistance and viscosity are achieved.

The composition may be sunscreen. Sunscreens are creams most often used on the skin in order to reduce the harmful effects of UV radiation. The use of mechanical MFC in sunscreens will make it possible to reduce or even eliminate the other UV blockers normally used in sunscreens today, e.g. titanium dioxide or zinc oxide.

The composition may be a coating color. Coating color comprising pigments, fillers etc is used for improving the printing properties of e.g. a paper or paperboard product. By adding mechanical MFC to a coating color the viscosity of the coating color will also improve. Thus, it is possible by the present invention to provide a coating color having both improved UV resistance and viscosity. The coating color comprising mechanical MFC according to the present invention may be added to a paper or paperboard product by any known conventional coating techniques.

The composition may be a sizing composition. Sizing compositions is normally used in paper or paperboard products to reduce the products ability to absorb water. Sizing compositions may be used as internal sizing, i.e. the sizing composition may be added to a furnish during production of the paper or paperboard product or it can be used as surface sizing, i.e. the sizing composition is added to the surface of the paper or paperboard product. The sizing composition may be added in by using any conventional sizing equipment.

The composition may also be a wood impregnation solution. Wood impregnation solutions are used to improve the characteristics of wood, e.g. to increase the strength, improve its' resistance to water, moisture or chemicals and/or to improve its' resistance against wood rot or other biological deteriorations. By adding mechanical MFC to a wood impregnation solution the treated wood will then also have improved UV resistance preventing the wood to be bleached or in any other way negatively affected by UV radiation. The wood impregnation solution may be added by any conventional method, e.g. by spraying the solution to the wood, dip the wood in the solution etc.

The composition may be a yarn. It is a big advantage in some fields to be able to make yarns having good UV blocking properties.

The composition may be a composite comprising a polymer, preferably a thermoplastic polymer material selected from the group comprising polyethylene, polypropylene, polylactic acid, polystyrene, polycarbonate, polyvinyl chloride, acrylonitrile butadiene styrene, ethylene vinyl acetate and/or derivates, and/or co-polymers, and/or mixtures thereof. The polymer content of the composition is preferably from 10 to 80 weight-% of the dry weight of the suspension of said fibrous material and said polymer material. It is of importance to provide composite materials used for example in screw caps with UV blocking properties.

Microfibrillated cellulose (MFC) shall in the context of the patent application mean a nano scale cellulose particle fiber or fibril with at least one dimension less than 100 nm. MFC comprises partly or totally fibrillated cellulose or lignocellulose fibers. The liberated fibrils have a diameter less than 100 nm, whereas the actual fibril diameter or particle size distribution and/or aspect ratio (length/width) depends on the source and the manufacturing methods. The smallest fibril is called elementary fibril and has a diameter of approximately 2-4 nm (see e.g. Chinga-Carrasco, G., i Cellulose fibres, nanofibrils and microfibrils: The morphological sequence of MFC components from a plant physiology and fibre technology point of view, Nanoscale research letters 2011, 6:417), while it is common that the aggregated form of the elementary fibrils, also defined as microfibril (Fengel, D., *Ultrastructural behavior of cell wall polysaccharides*, Tappi J., March 1970, Vol 53, No. 3.), is the main product that is obtained when making MFC e.g. by using an extended refining process or pressure-drop disintegration process. Depending on the source and the manufacturing process, the length of the fibrils can vary from around 1 to more than 10 micrometers. A coarse MFC grade might contain a substantial fraction of fibrillated fibers, i.e. protruding fibrils from the tracheid (cellulose fiber), and with a certain amount of fibrils liberated from the tracheid (cellulose fiber).

There are different acronyms for MFC such as cellulose microfibrils, fibrillated cellulose, nanofibrillated cellulose, fibril aggregates, nanoscale cellulose fibrils, cellulose nanofibers, cellulose nanofibrils, cellulose microfibers, cellulose fibrils, microfibrillar cellulose, microfibril aggregates and cellulose microfibril aggregates. MFC can also be characterized by various physical or physical-chemical properties such as large surface area or its ability to form a gel-like material at low solids (1-5 wt %) when dispersed in water. The cellulose fiber is preferably fibrillated to such an extent that the final specific surface area of the formed MFC is from about 1 to about 200 m2/g, or more preferably 50-200 m2/g when determined for a freeze-dried material with the BET method.

Various methods exist to make MFC, such as single or multiple pass refining, pre-hydrolysis followed by refining or high shear disintegration or liberation of fibrils. One or several pre-treatment step is usually required in order to make MFC manufacturing both energy efficient and sustainable. The cellulose fibers of the pulp to be supplied may thus be pre-treated enzymatically or chemically, for example to reduce the quantity of hemicellulose or lignin. The cellulose fibers may be chemically modified before fibrillation, wherein the cellulose molecules contain functional groups other (or more) than found in the original cellulose. Such groups include, among others, carboxymethyl (CMC), aldehyde and/or carboxyl groups (cellulose obtained by N-oxyl mediated oxidation, for example "TEMPO"), or quaternary ammonium (cationic cellulose). After being modified or oxidized in one of the above-described methods, it is easier to disintegrate the fibers into MFC or nanofibrillar size or NFC.

The nanofibrillar cellulose may contain some hemicelluloses; the amount is dependent on the plant source. Mechanical disintegration of the pre-treated fibers, e.g. hydrolysed, pre-swelled, or oxidized cellulose raw material is carried out with suitable equipment such as a refiner, grinder, homogenizer, colloider, friction grinder, ultrasound sonicator, fluidizer such as microfluidizer, macrofluidizer or fluidizer-type homogenizer. Depending on the MFC manufacturing method, the product might also contain fines, or nanocrystalline cellulose or e.g. other chemicals present in wood fibers or in papermaking process. The product might also contain various amounts of micron size fiber particles that have not been efficiently fibrillated. MFC is produced from wood cellulose fibers, both from hardwood or softwood fibers. It can also be made from microbial sources, agricultural fibers such as wheat straw pulp, bamboo, bagasse, or other non-wood fiber sources. It is preferably made from pulp including pulp from virgin fiber, e.g. mechanical, chemical and/or thermomechanical pulps. It can also be made from broke or recycled paper.

The above described definition of MFC includes, but is not limited to, the new proposed TAPPI standard W13021 on cellulose nanofibril (CMF) defining a cellulose nanofiber material containing multiple elementary fibrils with both crystalline and amorphous regions, having a high aspect ratio with width of 5-30 nm and aspect ratio usually greater than 50.

According to one embodiment the MFC may have a Schopper Riegler value (SR°) of more than 87. The Schopper-Riegler value can be obtained through the standard method defined in EN ISO 5267-1. This high SR value is determined for a repulped wet web, with or without additional chemicals, thus the fibers have not consolidated into a film or started e.g. hornification.

The dry solid content of this kind of web, before disintegrated and measuring SR, is less than 50% (w/w). To determine the Schopper Riegler value it is preferable to take a sample just after the wire section where the wet web consistency is relatively low.

The skilled person understands that paper making chemicals, such as retention agents or dewatering agents, have an impact on the SR value.

The SR value specified herein, is to be understood as an indication but not a limitation, to reflect the characteristics of the MFC material itself. However, the sampling point of MFC might also influence the measured SR value. For example, the furnish could be either a fractionated or unfractionated suspension and these might have different SR values. Therefore, the specified SR values given herein, are thus either a mixture of coarse and fine fractions, or a single fraction comprising an MFC grade providing the desired SR value.

Example

Chemimechanical softwood pulp was fluidized 10 times in a fluidizer to produce mechanical MFC.

MFC films comprising different amounts of mechanical MFC was produced. The mechanical MFC was mixed with chemical MFC to form films comprising less than 100% of mechanical MFC. The chemical MFC was produced by enzymatically treating kraft pulp with an endoglucanase enzyme at 50° C. for 3 hours followed by increasing the temperature to 90° C. to deactivate the added enzymes. The enzymatic treated pulp was thereafter fibrillated using a fluidizer at a consistency of 3% in order to produce chemical MFC.

The mechanical MFC and chemical MFC was mixed and formed to a MFC film. The transmittance of the films was measured using a Cary 100 Conc spectrophotometer with DRA CA-301 Integrating Sphere at room temerature and at a relative humidity (RH) of 50%.

The results from the tests can be seen in FIG. 1. FIG. 1 shows that the transmittance for the films comprising low amounts of mechanical MFC has low transmittance within the UV area and a high transmittance outside the UV area, e.g. in the visible light area. It is ideal to have low transmittance within the UV area and high transmittance in the visible light area. Thus, by the present invention it is possible to produce a transparent or at least semi-transparent film having good UV blocking properties, even at low addition of mechanical MFC.

In view of the above detailed description of the present invention, other modifications and variations will become apparent to those skilled in the art. However, it should be apparent that such other modifications and variations may be effected without departing from the spirit and scope of the invention.

The invention claimed is:

1. An UV blocking film comprising microfibrillated cellulose wherein at least part of the microfibrillated cellulose is microfibrillated cellulose produced from non-chemical modified lignocellulosic material wherein the film comprises 2.5-50% by weight of fiber based material of microfibrillated cellulose produced from non-chemical modified lignocellulosic material; and wherein at least part of the microfibrillated cellulose is microfibrillated cellulose produced from chemical modified lignocellulosic material wherein the film comprises 50-97.5% by weight of fiber based material of microfibrillated cellulose produced from chemical modified lignocellulosic material.

2. The film according to claim 1 wherein the non-chemical modified lignocellulosic material is mechanical pulp.

3. The film according to claim 2 wherein the mechanical pulp is chemithermomechanical pulp (CTMP), thermomechanical pulp (TMP), pressure groundwood (PGW) pulp and/or stone groundwood pulp (SGP).

4. The film according to claim 1 wherein the lignocellulosic material is fiber from coconut shell.

5. The film according to claim 1 wherein the film comprises 5-40% by weight of fiber based material of microfibrillated cellulose produced from non-chemical modified lignocellulosic material.

6. The film according to claim 1 wherein the film also comprises nano-fillers.

7. The film according to claim 1, wherein the film has a basis weight of less than 50 g/m2.

8. The film according to claim 1 wherein the film has a transmittance of at least 70% for radiation with wavelengths above 400 nm.

9. The film according to claim 1 wherein the film has a transmittance below 70% for radiation with wavelengths below 400 nm.

10. The film according to claim 1 wherein the film comprises 60-95% by weight of fiber based material of microfibrillated cellulose produced from chemical modified lignocellulosic material.

11. The film according to claim 1, wherein the film has a basis weight of less than 35 g/m2.

12. The film according to claim 1, wherein the film has a basis weight of less than 25 g/m2.

13. A method for manufacturing a film having UV blocking properties wherein the method comprises the steps of:
providing a first suspension comprising microfibrillated cellulose produced from non-chemical modified lignocellulosic material,
providing a second suspension comprising microfibrillated cellulose produced from chemical modified lignocellulosic material,
mixing the first and second suspension whereby a mixture is obtained,
wherein the mixture comprises the first suspension in an amount of 2.5-50% by weight of the fiber based material and the second suspension in an amount of 50-97.5% by weight of the fiber based material,
conducting the mixture to a wire and thereafter,
dewatering the mixture to form the film.

14. The method as claimed in claim 13, wherein the microfibrillated cellulose produced from non-chemical modified lignocellulosic material has a Schopper Riegler value)(SR°) of more than 87 SR °.

15. The method according to claim 13 wherein nano-filler is added to the first suspension and/or second suspension.

16. A composition having UV blocking properties wherein said composition comprises microfibrillated cellulose produced from non-chemical modified lignocellulosic material wherein the composition comprises 2.5-50% by weight of fiber based material of microfibrillated cellulose produced from non-chemical modified lignocellulosic material, and wherein said composition comprises microfibrillated cellulose produced from chemical modified lignocellulosic material wherein the film comprises 50-97.5% by weight of fiber based material of microfibrillated cellulose produced from chemical modified lignocellulosic material.

17. The composition according to claim 16 wherein the composition is a paint.

18. The composition according to claim 16 wherein the composition is a sunscreen.

19. The composition according to claim 16 wherein the composition is a coating color.

20. The composition according to claim 16 wherein the composition is a sizing composition.

21. The composition according to claim 16 wherein the composition is a wood impregnation solution.

22. The composition according to claim 16 wherein the composition is a composite comprising a polymer.

\* \* \* \* \*